(12) United States Patent
Bálint

(10) Patent No.: US 11,106,356 B2
(45) Date of Patent: Aug. 31, 2021

(54) SMART DEVICE WITH A DISPLAY THAT ENABLES SIMULTANEOUS MULTI-FUNCTIONAL HANDLING OF THE DISPLAYED INFORMATION AND/OR DATA

(71) Applicant: Géza Bálint, Dunavarsány (HU)

(72) Inventor: Géza Bálint, Dunavarsány (HU)

( * ) Notice: Subject to any disclaimer, the term of this patent is extended or adjusted under 35 U.S.C. 154(b) by 0 days.

(21) Appl. No.: 16/484,764

(22) PCT Filed: Feb. 23, 2018

(86) PCT No.: PCT/HU2018/050010
§ 371 (c)(1),
(2) Date: Aug. 8, 2019

(87) PCT Pub. No.: WO2018/154346
PCT Pub. Date: Aug. 30, 2018

(65) Prior Publication Data
US 2019/0369866 A1    Dec. 5, 2019

(30) Foreign Application Priority Data

Feb. 27, 2017   (HU) .................................. P1700089

(51) Int. Cl.
*G06F 3/0488*    (2013.01)
*B62D 1/04*    (2006.01)
(Continued)

(52) U.S. Cl.
CPC ......... *G06F 3/04883* (2013.01); *B62D 1/046* (2013.01); *G04G 9/0064* (2013.01); *G04G 21/08* (2013.01); *G06F 3/016* (2013.01); *G06F 3/04842* (2013.01); *G06F 3/04847* (2013.01); *G06F 2203/04808* (2013.01)

(58) Field of Classification Search
CPC .. G06F 3/04883; G06F 3/016; G06F 3/04842; B62D 1/046; G04G 9/0064; G04G 21/08
See application file for complete search history.

(56) References Cited

U.S. PATENT DOCUMENTS 6,096,984 A * 8/2000 Howell ................. G06F 1/1616
178/18.01
2009/0244092 A1* 10/2009 Hotelling .............. G06F 3/0304
345/619

(Continued)

*Primary Examiner* — Roland J Casillas
(74) *Attorney, Agent, or Firm* — Handal & Morofsky LLC; Anthony H. Handal; Izick Vizel

(57) ABSTRACT

Arrangement for the controlled manual selection of an image and/or the adjustment of the display parameters thereof to be shown on a display (13, 22) of a smart electronic device that comprises a handling field (2, 25, 32, 41) controlled by the touch of a finger, wherein a first predetermined group of image and/or display parameters can be controlled by a finger of a user, and the arrangement comprises a further handling field (1, 27, 37, 38, 42) arranged in a position that can be touched by a different finger of the same user and by being touched at least one further display parameter can be adjusted that does not belong to the first group, and the further handling field (1, 27, 37, 38, 42) is arranged spaced from said handling field (2, 25, 32, 41) and the handling fields are mechanically connected through a common body (11, 24, 31).

10 Claims, 7 Drawing Sheets

(51) Int. Cl.
*G04G 9/00* (2006.01)
*G04G 21/08* (2010.01)
*G06F 3/01* (2006.01)
*G06F 3/0484* (2013.01)

(56) References Cited

U.S. PATENT DOCUMENTS

2011/0087963 A1* 4/2011 Brisebois .............. G06F 3/0485
                                                                715/702
2014/0292692 A1* 10/2014 Okuyama .............. B60K 37/06
                                                                345/173
2016/0085397 A1* 3/2016 Jain ........................ G06F 1/163
                                                                715/828

* cited by examiner

SPREAD (ZOOM IN)

PINCH (ZOOM OUT)

SWIPE

ROTATE RIGHT

ROTATE LEFT

PAN
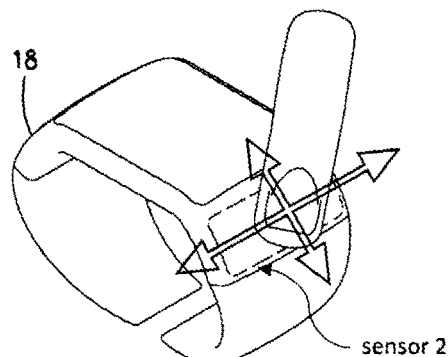
Fig. 10
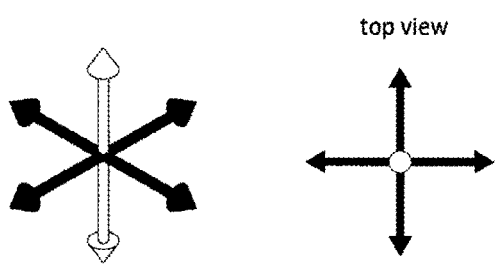
ROTATE „TOP"
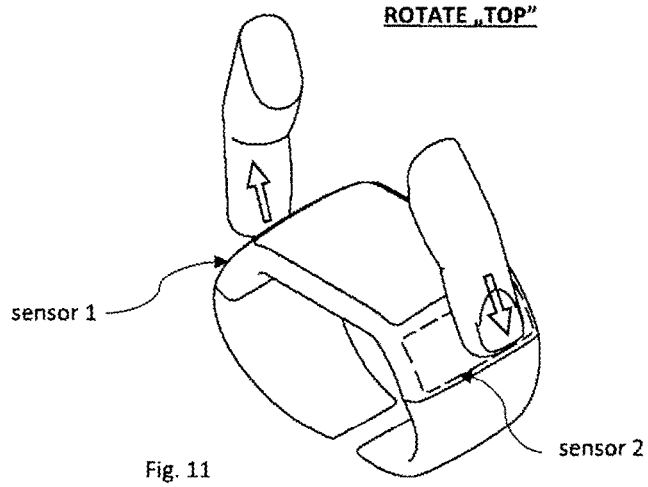
Fig. 11
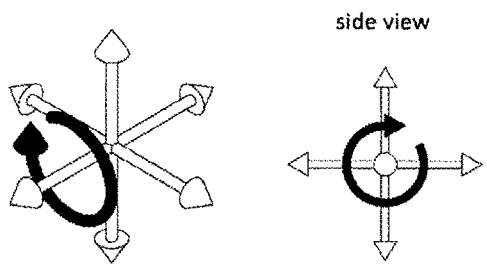
ROTATE „BOTTOM"
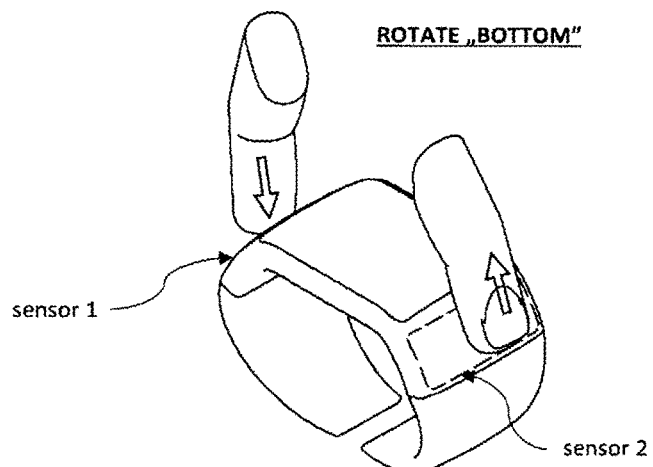
Fig. 12
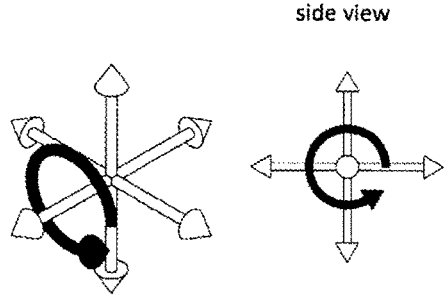

SMART DEVICE WITH A DISPLAY THAT ENABLES SIMULTANEOUS MULTI-FUNCTIONAL HANDLING OF THE DISPLAYED INFORMATION AND/OR DATA

The invention relates to an arrangement for the manually controlled selection and/or adjusting the display parameters of a picture to be displayed on the display of an intelligent electronic device, which has a handling field controlled by the touch of a finger by which a first predetermined group of the picture and/or the parameters of the display can be controlled by a finger of a user.

It is a known fact that the fast development of computing devices has provided such high processor and data storage capacities that made possible the realization of several kinds of smart devices that all have small sizes. Such devices are primarily mobile phones provided with more and more functions in which the use as a phone requires only a small part of their capacities, or the smart watches which have performance competing with those of such mobile phones, furthermore specific smart devices serving different tasks. Devices that can be built in cars belong also to such devices which can perform several tasks in addition to their use for navigation.

Such devices require that their user can choose among the ever higher choice of possibilities or to make use of the power provided by such devices, whereas the size of the human hand and fingers and their anatomical limitations or other circumstances (e.g. the other tasks of the hands at car drivers or the need of holding the device) impose human limits to the miniaturization also from the point of view of handling the devices and choosing from the multiple number of functions.

Such a limit is e.g. the design of the keyboard required for the entry of the data, wherein the miniaturization requires manipulation in ever smaller fields. As far as the data entry is concerned one direction of the development is the perfection of voice recognition which might replace manual data entry to a certain extent, or the invention of solutions in which the smart recognition of small finger movements can provide a direct data entry, but here the user has to learn predetermined gesture combination. Such a system can be learned from the publication WO2016/170374 A1 wherein a new paradigm system has been provided for direct data entry. Here two alternative solutions have been suggested for the sensing of the same gesture combinations. In one of these a part or the whole handling surface of the device can be moved to a slight extent relative to the body of the device along two mutually normal directions. The displacement is limited by a closed path (preferably circular or elliptical), and along this path, preferably at diametrically opposite positions recesses or blocks are arranged which can be easily sensed by the finger of the user by touching or by haptic feedback. The reaching of the edge of the path can also be sensed. The handling field is brought by a biased spring system always to the centre of the field, therefore the entry of a character can take place by the drawing of a combination of gestures that can be easily learned and sensed. In the other embodiment using the same principle the entry field is stationary but it comprises a similar path of a kind of recess along which the finger can be moved. The special locations can be recognized either by recesses placed at such locations or by small swelling isles that can be sensed by the tip of the finger. It is characteristic to both of these alternatives that the "drawing" of the characters take place in the same way and this operation is always associated with a haptic feedback, i.e. for the drawing of the characters the user need not observe a display field or to check the finger movement by visual observation.

The control of the picture shown on the display according to the needs of the user represents tasks which gets more and more complex just because of the increased number of possibilities and users requirements. In case of touch screen devices several display functions can be realized by gestures made in different directions including the shifting of the picture in both directions, increasing or decreasing the scale or the rotation of the picture. A common drawback of these solutions that they take a non-negligibly small area from the display field which itself is also small. The problem increases with decreasing display sizes.

The development of requirements needs picture handling that surpasses the listed possibilities. A typical example for such requirements is the visualization in 3D which is needed in ever more applications. The three dimensional data of the object to be displayed are available in the memory of the device, but the user might need to shift the picture in one or more of three mutually normal directions, to rotate it around any axis and to magnify or scale down its size. A similar task which cannot be resolved in a two-dimensional plane lies in if during a navigation the map of the given areas should be observed from different aspects, e.g. where the selected type of the points of interest (POI), where traffic boards or height lines or surrounding establishments are needed to be observed more closely. These differing display contents are arranged in layers, and for the picture control there is also a need to move between the layers.

A further group of picture handling parameters do not relate to 3D tasks but to optimum performance of searching (scroll) tasks, in which first a smaller field is searched in a larger one, and when we approach to the target the enlarged picture should be moved much slower. This means that in a movement along a parameter (left-right or up-down movements) one has to be able also to change the searching speed. From the side of the requirements there is a need to change a high number of parameters, whereas in the two-dimensional field which has ever smaller size the number of parameters that can be handled is limited and the tasks can be solved e.g. by the association and use of several function fields.

The object of the invention is a better utilization of the human side of such a man-machine system and to provide picture control and handling possibilities by which the group of parameters that could be well handled by the previously used two-dimensional control can be broadened by creating adjustment possibilities for further parameters.

A further object of the invention lies in that the broadening of the possibilities do not make the user more tired, but he can carry out the required adjustment in a comfortable, almost automatic way.

A further objet of the invention is to provide further handling fields which do not take valuable parts from the available display surface or at most only small areas.

A still further object of the invention is to optimize the previously set objects to discrete important fields of applications (smart watches, car applications, using in mobile devices) by taking into account the limitations of such specific applications.

A still further object of the invention is to provide during the provision of the enlarged picture handling and picture controlling tasks the use of the aforementioned direct data entry functions also for picture handling and control.

These objects have been reached by providing an arrangement for the controlled manual selection of an image and/or the adjustment of the display parameters thereof to be shown on a display of a smart electronic device that comprises a handling field controlled by the touch of a finger, wherein a first predetermined group of image and/or display parameters can be controlled by a finger of a user, and according to the invention the arrangement comprises a further handling field arranged in a position that can be touched by a different finger of the same user and by being touched at least one further display parameter can be adjusted that does not belong to the first group, and the further handling field is arranged spaced from said handling field and the handling fields are mechanically interconnected through a common body.

For imitating the natural 3D movements it is preferred if said handling fields close an angle with each other or they are arranged on opposing surfaces of the body.

For the utilization of a known direct data entry solution the handling field or a part thereof can be moved relative to the body along a closed path in two mutually normal directions, and such a design of the handling field constitutes in a first functional mode an element of an in itself known data entry device, and in a different other functional mode such movement relative to the body is associated with further display parameters.

The learning of the entry will become easier if the simultaneous movements of two fingers on said handling field and said further handling field are coordinated with each other according to a predetermined logical system and such movements result in image movements logically connected with the same logical system.

A special image handling possibility will be provided when the first and second groups of display parameters comprise together the parameters required for the adjustment of the image along three mutually normal coordinates x, y, z.

In an important field of application the body is constituted by the body of a smart watch that can be placed on the wrist of the user, and said handling field is arranged close to an end of a display and the further handling field is arranged close to the other end of the display.

The overall size can be decreased if the further handling field is substantially smaller than said handling field.

In a further important application the body is constituted by a part of the steering wheel of a car.

In this case it is preferred if said handling field is placed within the reach of a finger of a hand when gripping the steering wheel and it is facing the driver, and the further handling field is arranged at the reach of a further finger of the same hand and facing in opposite direction.

In a further expedient field of application the body is constituted by a flat rectangular body of a smart electronic device and said handling field is arranged on the front face of the device that front face comprises the display of the device, and the further handling field is arranged on the rear face of the device, and said handling field comprises a means ensuring the entry of data by haptic feedback either by moving the means or a finger along a closed path by gesture combinations, whereas by the same means that comprises the closed path in a further mode of operation further image display parameters can be controlled.

In a further possible field of application the handling field and the further handling field are provided on a body or bodies that can be tilted out into the space from a planar handling surface of a laptop or tabloid provided with a keyboard.

The arrangement according to the invention provides a full solution of the tasks set and its use provides a substantially enhanced and simplified handling compared to the previously known solutions.

The arrangement according to the invention will now be described in connection with exemplary embodiments thereof in more detail, in which reference will be made to the accompanying drawings. In the drawings:

FIG. 10 shows the sketch of the movement in the plane x, y;

FIG. 11 shows the sketch of the rotation around the axis x in one direction;

FIG. 12 shows the sketch of the rotation around the axis x in the other direction;

The first embodiment of the device according to the invention is a smart watch 10 which has a large arced body that follows the shape of the lower arm (wrist), coupled through pivotal connection to a metal strap 12 of matching style that can be released or opened and this ensures the comfortable wear of the watch 10 on the lower arm. A miniature electronic system is arranged in the interior of the smart watch 10 that has an internal structure and processing power comparable to those of state-of-the-art smart mobile phones and can provide substantially the same functions, moreover in the present case additional functions that could not be realized with conventional flat hand held mobile phones. The essence of the invention does not lie in the internal design of the smart watch but the solution by which this miniature electronic device can be handled by its user in a more comfortable, faster and at the same time more efficient way.

Figure 1:
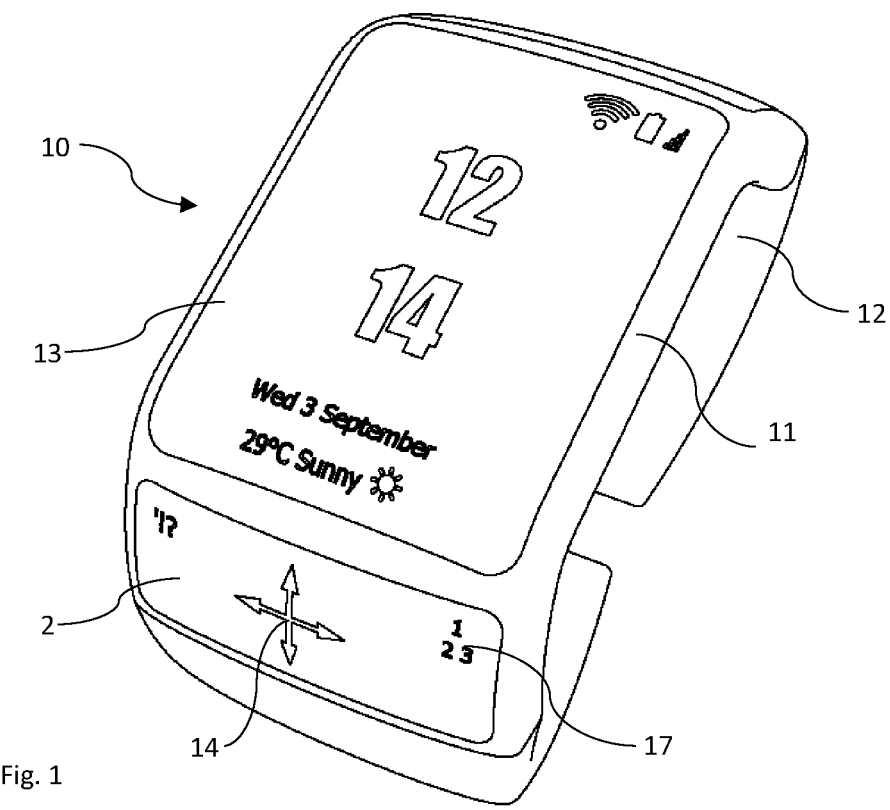
FIG. 1 shows the perspective view of a smart watch seen slightly from below.
Figure 2:
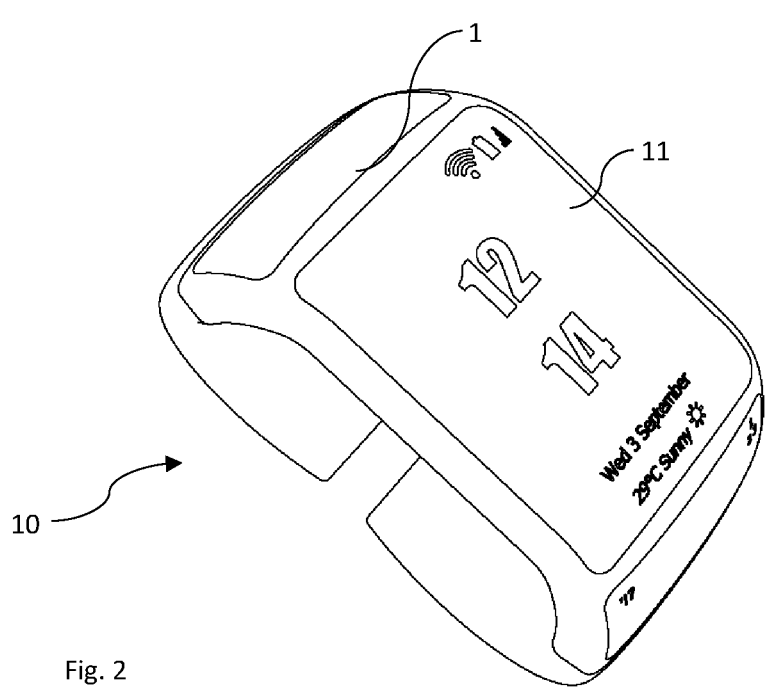
FIG. 2 is a view similar to FIG. 1 seen slightly from above.

The largest central field of the watch 10 is a slightly arced display 13 which is preferably but not necessarily touch sensitive. The watch 10 is shown in FIG. 1 slightly from below and FIG. 2 slightly from above. Over and under to upper edge of the display 13 (as shown in FIG. 2) a first handling field (sensor) 1 is arranged that has a handling surface which is touch sensitive and has a narrow shape which is elongated in horizontal direction and forms a rectangle that extends practically along the full width of the watch 10.

Under the display 13 a second handling field (sensor) 2 is arranged which can well be seen in FIG. 1 that has a width which is preferably equal with the width of body 11 of the watch 10, but has a height greater than the height of the first handling field 1 therefore it has a substantially larger surface.

Figure 3:
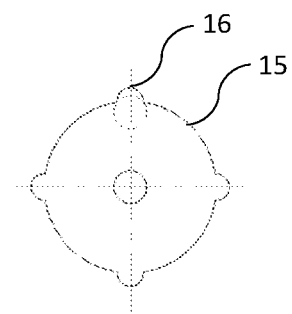
FIG. 3 is an enlarged sketch visualizing the movable property of the handling field 1.

In a preferred embodiment the second handling field 2 is a flat mechanical unit that can be slightly displaced relative to the body 11 of the watch 10 parallel to itself (but in no case turned) along two mutually normal axes visualized in FIG. 1 by double arrow 14. The mechanical connection between the handling field 2 and the body 11 and the associated functions take place as disclosed in the publication WO/2016/170374 A1, i.e. the handling field 2 can be moved by a single finger in a manner limited by a closed path 15 shown in FIG. 3 and that movement provides a haptic feedback and enables a data entry which can be learned in an easy way. For facilitating the haptic feedback in diametrically opposite sides of the path 15 respective small recesses 16 are formed, whereby during use one can sense when during the movement along the path 15 the respective recesses 16 are reached. The possibility of such kind of moving the handling field 2 enables the direct data entry described in the referred publication. It should be noted that the actual size of the path 15 shown in FIG. 3 is much smaller and the length of the diameter of the displacement is at most a few millimeters. Otherwise the surfaces of the handling fields 1 and 2 are sensing surfaces therefore finger movements along the surfaces are sensed by appropriate electronic units, and the respective movement gestures can be distinguished from each other according to their directions, speed, sizes and locations. Because the handling surface 2 is substantially larger than the other one, by moving our fingers along this surface more detailed and complex gestures can be made.

It should be noted that the movement of the handling field 2 along the path 15 shown in FIG. 3 takes place against a spring bias, therefore the user can well distinguish if he/she moves a finger along the stationary surface (as if it had been only caressed) or if the whole handling field 2 was pushed by force and moved which is required for the data entry.

Because the handling field 2 is used for different purposes on it (preferably on its upper part) several small function zones are shown, of which in FIG. 1 function zone 17 has been shown that is associated with numerical entries. In default state the sensor entry function of the handling field 2 is set and the data entry function will be triggered if the handling field 2 is pushed and fully moved with respect to the body 11. In this starting state the data entry is e.g. adjusted to the entry of the characters of the English alphabet, but following a previous pressing of the function zone 17 the respective movement combinations will be associated with numbers or punctuation marks, and further functional zones can be assigned to different word processing commands or states. These possibilities are described in detail in the cited publication, and from the point of view of the present invention it has only significance that in a stronger pressed state the handling field 2 can also be used for the entry of data and commands.

In case the present invention is used for the smart watch 10 then it is important to note that the handling fields 1 and 2 are not only characterized by the facts that they are arranged at a distance from each other e.g. at the two ends of the display 13 but it is also important that their respective planes close an angle which facilitates for the user the process of spatial control to be described later. It is also important to note that the distance and arrangement of the handling fields 1 and 2 enable that they can be easily touched by two fingers without any physical effort, whereby they can be contacted by the fingers separately or together so that the fingers can be comfortably moved along them.

Figure 4:
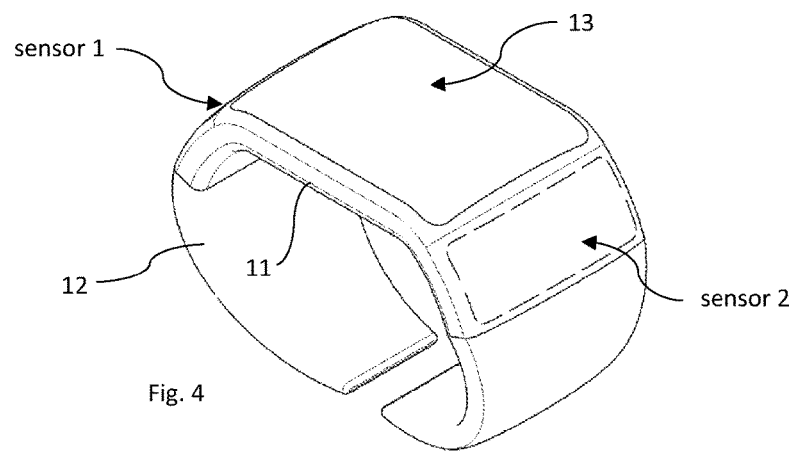
FIG. 4 shows the simplified perspective view of the smart watch seen from a different direction.

FIG. 4 shows a simplified perspective view of the smart watch 10 in which the relative angle closed by the handling fields 1 and 2 is better illustrated. For rendering the understanding of the respective functions easier, the basic properties of these functions have been shown in FIGS. 4 to 12 by their English terms.

Reference is made now to FIGS. 5 to 12 which illustrate the realization of respective main functions. Because the handling takes place in the space i.e. in three dimensions, beside the respective figures the directions x, y and z of a spatial coordinate system is always indicated and right beside the coordinates the projection in the x-y plane is shown, and those coordinates are drawn with heavy lines along which the given function (movement combination) can control the movement of the picture or cursor shown on the display 13. It is supposed that the processor in the smart watch 10 comprises the spatial data of the given function and it is able to display them. Such can be e.g. in case of maps the display of the map itself in the x,y plane, and at the same time (as it is known) there are properties which can be visualized in respective different layers (e.g. different points of interest, traffic boards, rules, height lines, etc.) because their simultaneous indication would render the picture too complex for interpretation. There are further functions and programs when the inner coordinates of a body or product are available in the machine (e.g. in case of 3D planning), and it is important that the user can see the structure not only in the x,y plane but examination in the depth i.e. along the axis z should also be made possible i.e. the interested picture can be selected. The solution according to the invention provides an easy way of handling this rather sophisticated task so that during the handling the fingers and the hand will not cover the area of the display 13.

Figure 5:
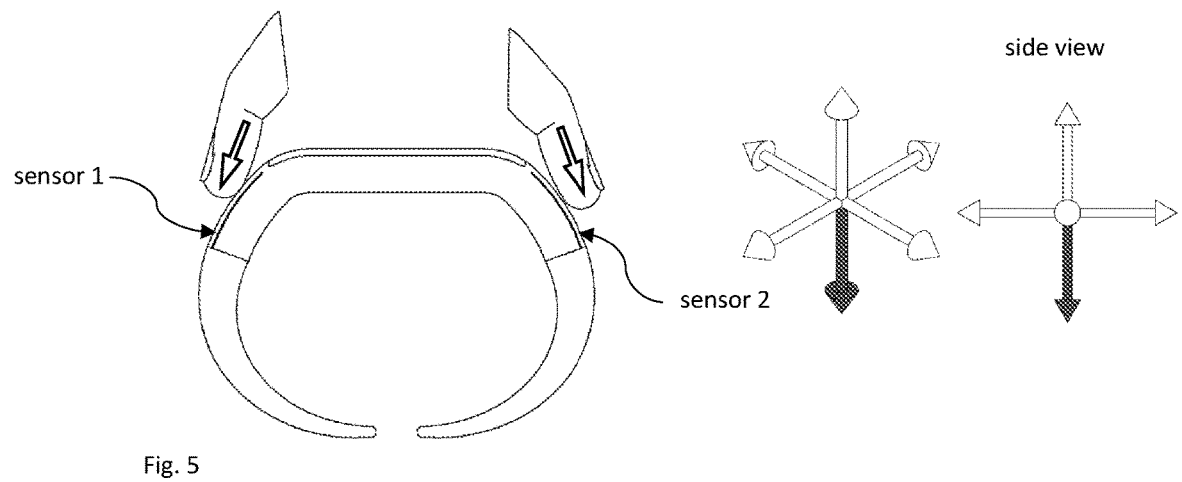
FIG. 5 shows the sketch of the downward movement along the axis z.

FIG. 5 illustrates the downward movement along the axis z (spread). To such movement the two fingers should be moved downward along the handling fields 1, 2 as shown by the arrows in the drawing. Then we move downward in depth from layer to layer. Because the watch 10 is worn most often on the left wrist, the downward movement of content in the space represents a natural imaging by the brain to slide the two fingers downward therefore such a control utilizes the movement combinations which is the most natural one for the user.

Figure 6:
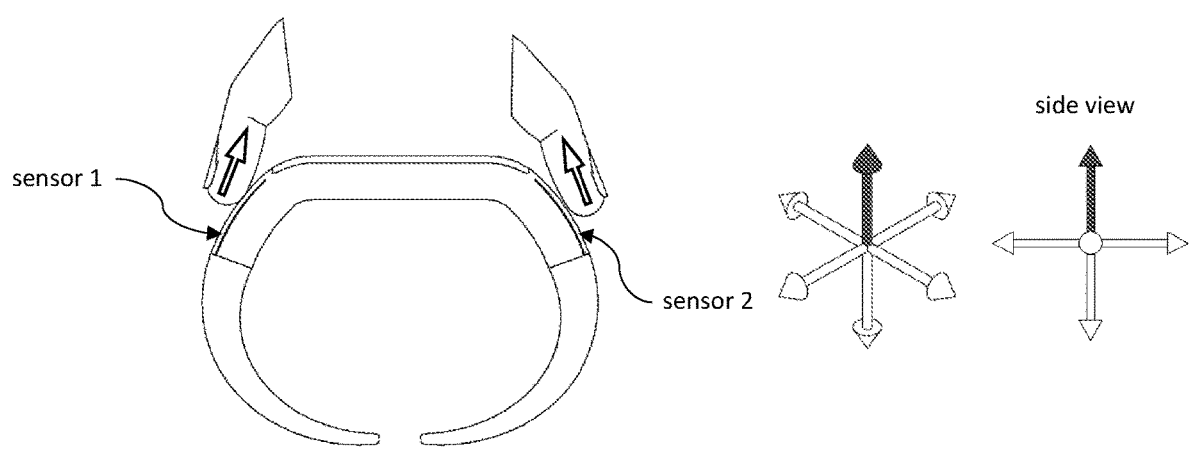
FIG. 6 shows the sketch of the upward movement along the axis z.

FIG. 6 shows the opposite upward movement (pitch) along the axis z which is just the opposite of the previously described movements.

Figure 7:
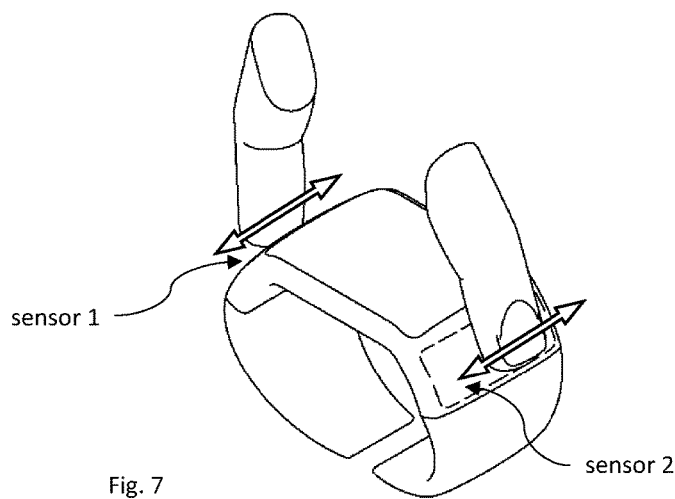
FIG. 7 shows the sketch of the movement along the axis x.
Figure 7:
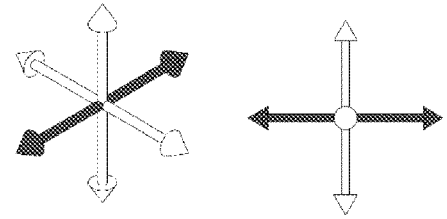

FIG. 7 shows the shifting of the image in the plane x-y in the direction x (called as swipe) in case of a control with two fingers in both directions. It should be noted that in the actually displayed plane the basic movements (shifting from right to left and up and down, and the magnification or downsizing the image) can also be realized by the planar control of the handling field 2, but if the user has got used to control the position of the displayed image then it is worthwhile to ensure the control of such movements by two fingers.

Figure 8:
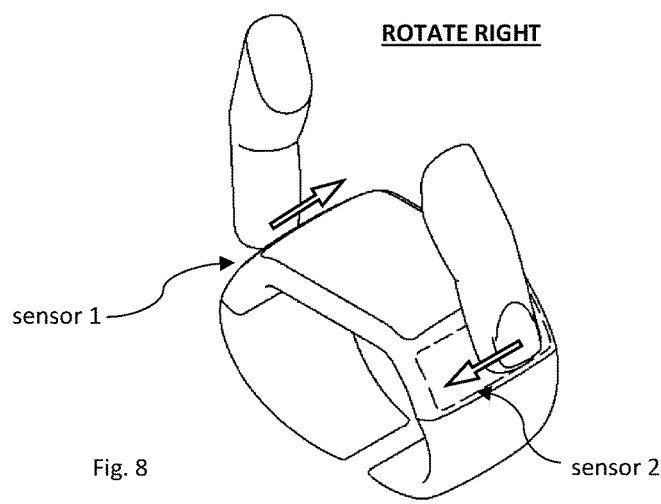
FIG. 8 shows the sketch of the clockwise rotation movement around the axis z.
Figure 8:
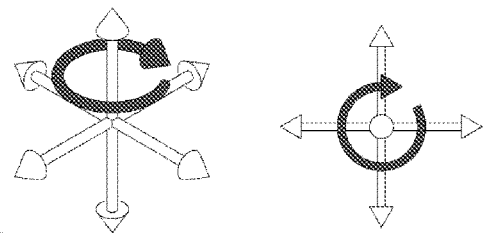
Figure 9:
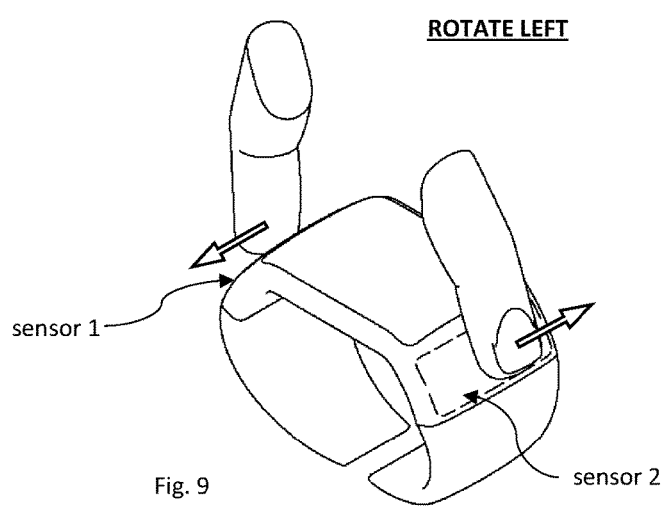
FIG. 9 shows the sketch of the rotation around the axis z in the other direction.
Figure 9:
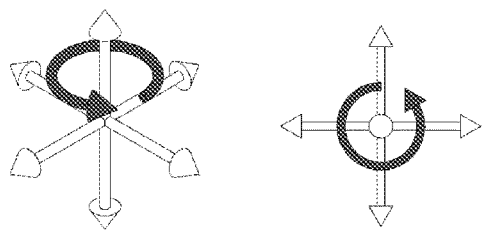

FIG. 8 shows the control of rotation around the axis z in clockwise direction, while FIG. 9 shows a similar control in counter-clockwise direction. The finger movements associated with the rotation correspond again to the natural ways because the fingers are moved in opposite directions.

FIG. 10 shows the previously mentioned movement with a single finger in which there is a need of moving the finger only along the handling field 2. This kind of movement (pan movement) that takes place in a given image plane is used most often. Therefore such movement can be supported by a plurality of functions. When the image or the cursor should be moved in the displayed plane, then the searched position is searched first with a coarser movement and when the target will be visible, the speed of the movement should be decreased. The term "speed" is interpreted by the displacement on the screen associated with a unity finger displacement. For the changing of the speed the existence of the other handling field 1 provides a good possibility. If the handling field 1 is touched with a different finger at a stable position 18, then this contact will be sensed by the processor in the watch 10 as a control event for changing the speed. In several instances it is sufficient if only a single speed changing step is provided, and in such cases it is enough if the position 18 is simply touched. In systems with several speeds the control can be made by multiple subsequent contacts and the change in reverse direction can also have several ways. One of such possibilities lies in if the right side of the handling field 1 is touched then the speed will decrease and if the left side is touched, the speed increases. In an alternative possibility the position of the contact has no role but e.g. the first three contacts increase the speed and each subsequent contacts decrease the same. The essence does not lie in the way how the changing of the speed takes place but in the fact that the speed changing is enabled by the touching of the other handling field 1.

Finally, FIGS. 11 and 12 show the control of rotation in the y-z plane (i.e. around the axis y) which is just as natural for the user as it was in the x-y plane.

Besides the control with two fingers the functions used and learned in previous devices can still be used, i.e. if two fingers are moved away along the larger handling field 2 then the image will be magnified and if the fingers are moved towards each other then the image will be smaller.

A further interesting possibility is obtained if the handling field 2 is moved relative to the body 11, i.e. the shifting of the displayed image in the given plane is controlled by one finger to take place upwards and downwards or right to left and this possibility corresponds to the scroll function. When the display is controlled in this way, the handling field 2 is not in data entry mode, thus the handling field 2 can be moved to any one of the special positions defined by the four recesses 16 along the path 15 shown in FIG. 3. These positions can be associated e.g. with the respective ones of the movements in upward, downward, right and left directions. The processor in the watch 10 can also be programmed in such a way that in display control mode the placement of the handling field 2 to any one of the recesses 16 will move (shift) the displayed image in the associated direction which means the simple realization of the scroll function to up-down and left-right directions without the need of any separate handling means. It should be noted that the possibility of moving the handling field 2 relative to the body 11 can be associated with further display control functions by associating respective gestures with appropriate display control functions that can be easily interpreted. For instance a clockwise rotation gesture along the path 15 can result in the rotation of the image to the right and a gesture in the opposite direction causes the rotation of the image to the left. Therefore, according to the invention the conventional control in a single plane is enhanced first by the control using two handling fields as shown in FIGS. 5 to 12, and this can be combined or complemented with the possibility of moving the handling field 2 relative to the body 11 and utilizing the presence of the special positions, whereby further display functions can be realized which increase the degree of freedom of handling and also increase its comfort.

Figure 13:
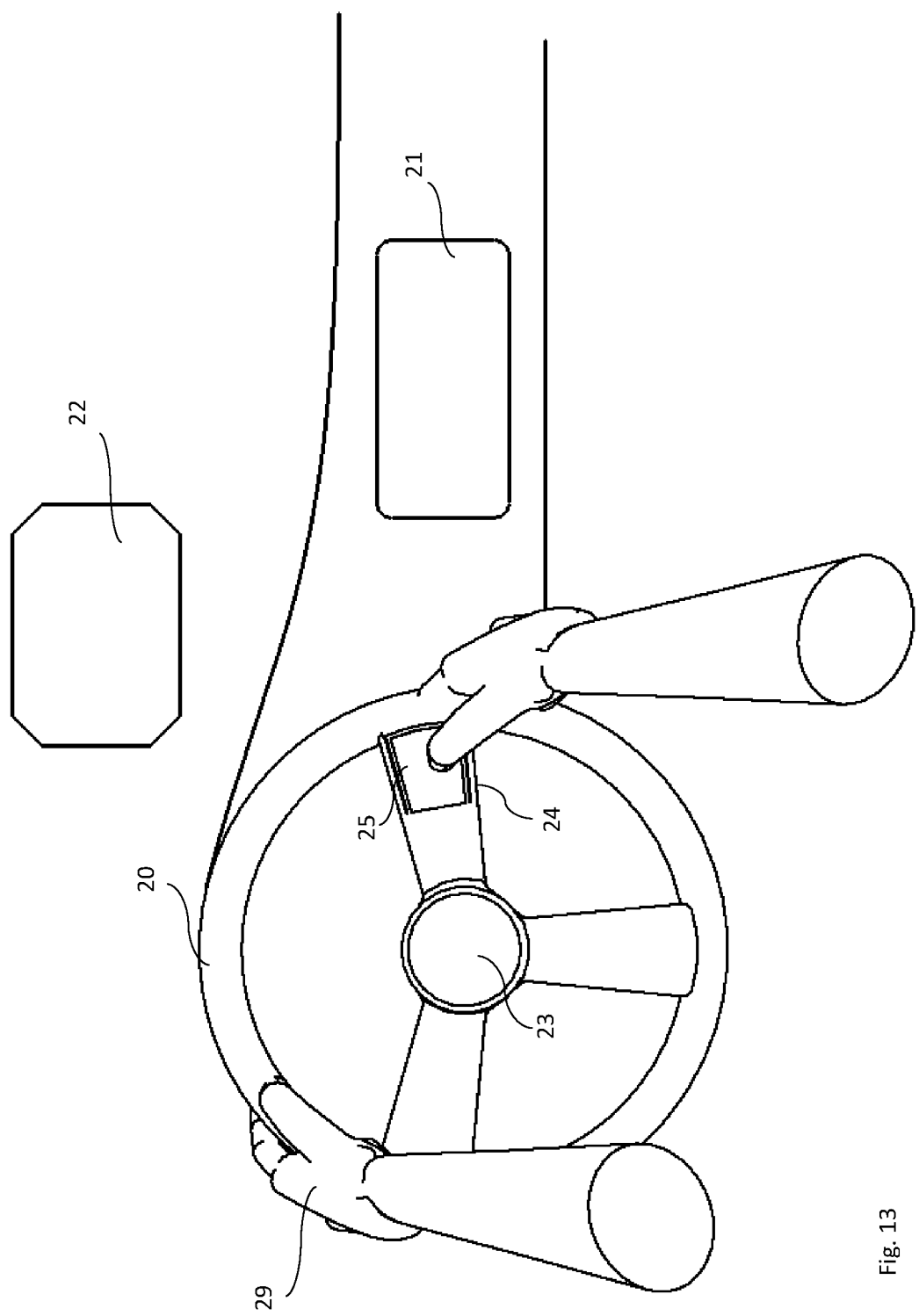
FIG. 13 shows a detail of the inner space of a car with the steering wheel and parts of the dashboard and the windshield.

The three-dimensional control of the image and/or the cursor by multiple fingers cannot be utilized only in case of smart watches but also in several other fields of applications. FIG. 13 shows a detail of the inner space of a car in which steering wheel 20 is gripped by both hands of a driver. In the inner space of the car one can see the usual handling and display means of which a built in display 21 is mentioned and before the windshield a projected image 22 can be seen generated by the projector of a smart electronic control unit built in the dashboard. The image 22 can show a detail of a route map. The task of the control according to the invention is the three dimensional control of the displayed image 22 projected for the driver by the aforementioned and not illustrated control unit in a similar way to what was explained in the previous embodiment. The steering wheel 20 of the car and its central part 23 fixed to the steering column are generally interconnected by two connection members 24 of which one is close to the right hand of the driver and the other one is close to the left hand. Depending on whether the driver is right- or left handed, on the front surface of the right or left connection member 24 a handling field 25 using sensors is arranged which can be designed and controlled in a similar way as the handling field 2 of the smart watch 10 in the previous example. The difference lies in the larger available surface which might render unnecessary that the whole handling field 25 be designed in a movable way as it was the case at the handling field 2 to solve thereby the data entry tasks. In this case a different type of data entry might be more preferred which is described as the second data entry mode in the document WO/2016/170374 A1, in which not the handling field is moved along a closed path but a closed path is made on the surface and the recesses that enable touch sensing of the diagonally opposite positions are arranged at the edge of the path. This inner field is divided by slightly outwardly swelling isles into a plurality of parts, preferably four parts, and in such a case the data entry can be made with the same movement combinations when the whole field was moved along the path, but in the present case the finger has to be moved on the stationary field. It is only a question of details whether the data entry field is provided on a separate part of the handling field 25 or it is arranged beside it or at any convenient place.

Figure 14:
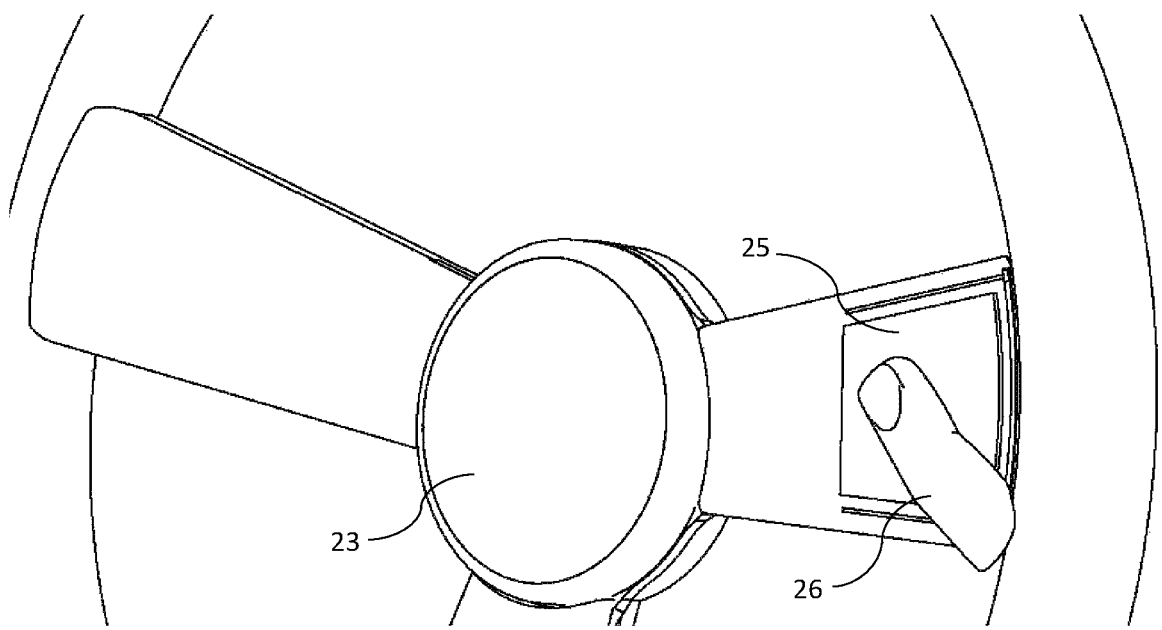
FIG. 14 is a sketch illustrating the handling of a first handling field that faces the driver.
Figure 15:
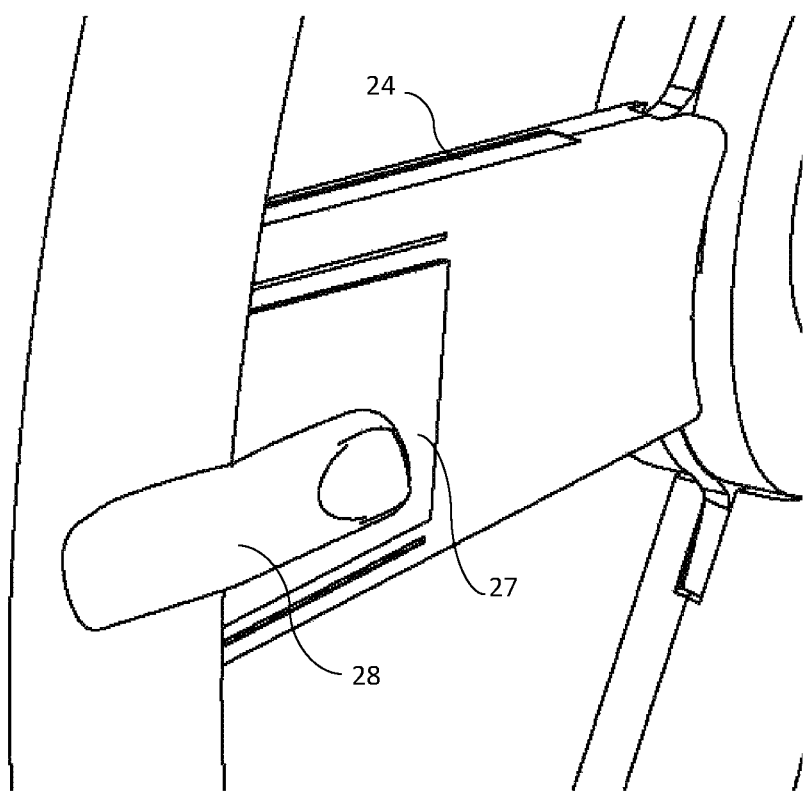
FIG. 15 is the sketch of a second handling field facing away from the driver.

In the enlarged views of FIGS. 14 and 15 the front part of the connection member 24 of the steering wheel (FIG. 14) and the rear part (FIG. 15) thereof have been shown. FIG. 14 shows the enlarged view of the front handling field 25 facing the driver as being touched by the thumb 26. FIG. 15 shows the rear surface of the connection member 24 which is more away from the driver on which a rear handling field 27 is provided and having sensors, and being touched by the forefinger 28 of the driver.

For controlling the image and/or the cursor projected or shown on the display 21 the same movement combinations can be associated as they were shown and explained in connection with FIGS. 5 to 12, thus all kinds of movements along or around the axes x, y, z can be controlled by the easily coordinated movement of two fingers of the driver. Although it is preferred if the two front and rear handling fields 25, 27 are arranged behind each other and can be controlled by two fingers of the same hand, a different solution can also be possible, in which the second handling field 27 is provided on the front surface of the other or a further connection member of the steering wheel 20, then this can be controlled by a finger of the left hand 29 of the driver (FIG. 13).

The previously mentioned data entry function can be realized according to both versions of the previously referred publication. The front handling field 25 can be made movable relative to the connection member 24 of the steering wheel similar to the movement of the handling field 2, and in that case similar functional possibilities will be available. Alternatively, as described above, it is possible that the closed path is provided on a part of the front handling field 25 and the movement of the finger on that field provides either the data entry or the special image movement functions. In the embodiments described so far the structure on which the handling fields were provided have not required special holding by a hand because the watch 10 was fixed on a hand and the fingers of the other hand could freely move thereon. In the application in the car the handling fields were held by the steering wheel, and the fingers of the hands holding the steering wheel could move along the fields in an easy way.

One of the most frequent needs for the three dimensional control or for the enhancement of handling functions present itself in case of handling elements of smart mobile phones or other intelligent electronic devices. In such cases the free movement of the fingers is limited by the need of holding the device itself by a hand, i.e. the hand has multiple tasks, and without the danger of dropping the device the movement of the fingers is far less free as in the previous cases.

Figure 16:
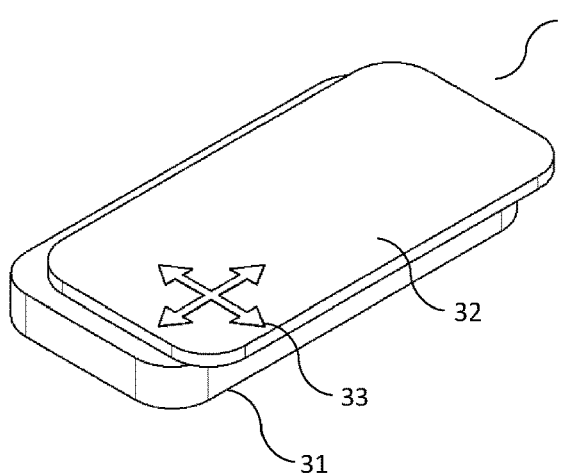
FIG. 16 is the perspective view of a smart mobile device wherein the full display field can be moved.
Figure 17:
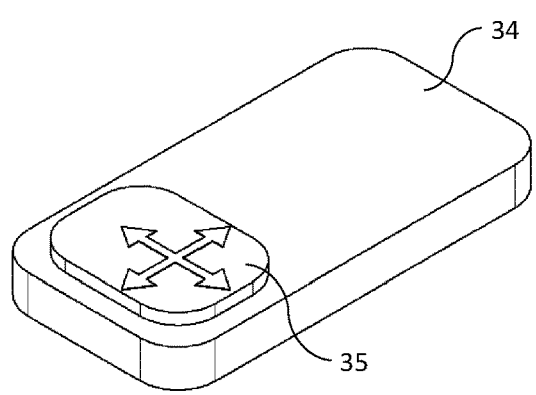
FIG. 17 is a view similar to FIG. 16 wherein the handling field takes only a small part of the upper surface of the upper surface.

In FIGS. 16 and 17 respective typical smart mobile devices are shown which are basically equipped with the data entry handling fields as described in the previously referred publication WO/2016/170374 A1. Device 30 shown in FIG. 16 has a flat rectangular body 31 which is almost fully covered by a handling field 32 which is at the same time a touch screen display. The handling field 32 can be moved within certain limits along the respective directions of double arrow 33 as it is described in detail in the publication. Device 34 shown in FIG. 17 differs from that only in that it has only a smaller handling field 35 which can also be moved in both directions within certain limits and leaves most part of the front surface of the device 34 free, on which also a touch screen display is provided. The surface of the handling field 35 is at the same time a sensor surface which can sense the movement of the finger that contacts it. The handling field 35 can be used naturally also for data entry as described in the referred publication.

Figure 18:
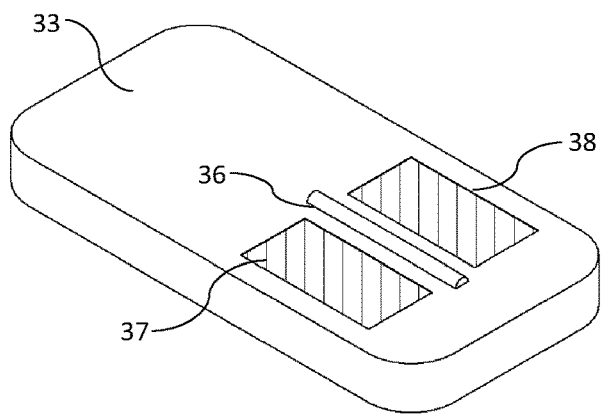
FIG. 18 is a sketch showing the rear plate of the mobile device.

FIG. 18 shows the rear side of the pervious devices 30, 34 on which preferably in the central part a ridge 36 swells out slightly of the surface which is parallel with the longitudinal axis of the device. On both sides of the ridge respective handling fields 37, 38 are provided. When the device is held by a hand, a thumb can be moved freely the front handling field 32 or 35 provided on the front side of the device, and a further finger can move along the rear surface without the danger of dropping the device, but this movement will not be as fine and sophisticated as if the finger had no other task because the holding function imposes limitations. One of the fingers touching the rear side will have such a degree of freedom to feel the presence of the ridge 36 and can distinguish whether it contacts the fields 37 or 38 at the right or left side of the ridge 36.

In such devices the handling field on the front face will be used again in multiple ways, i.e. if it is pressed slightly and displace it along the directions x or y relative to the body 31 of the device 30 or 34, then the data entry function will be selected and with the movement data entry can be made.

When the finger is moved on the handling field 32 or 35 with such a small force that it cannot move away from its biased basic position, then with the movement of the finger a pan control can be realized as shown in FIG. 10. If at the same time e.g. the left handling field 37 from the ridge 36 is touched (i.e. there is no need to move the finger bound by holding the device) then a change in function will take place, and by moving the handling fields 32 or 35 further movement functions can be selected. The handling field 32 or 35 can be moved by radial displacement from the central position to any of the recesses 16, can be pushed to these recesses or can be moved along the closed path with making different gestures. To these positions and gestures respective image or cursor control functions can be associated, e.g. if the handling field is pressed to the upper recess along the axis y then the image can be moved in upward or oppositely to downward direction, and pressing it to the ends of the transversal diagonal the image can be shifted to the left or right, and a clockwise arc gesture results in a rotation to the right and a gesture in the opposite arc results in a rotation to the left. An interesting combination can be reached e.g. if the handling field is pressed to a vertical recess then the image moves upwards and if in that case the pressure is decreased but the finger is moved in the same vertical direction along the sensing field then the initiated vertical image movement can be continued until the finger is removed or lifted.

In case the finger at the rear side is not touched to the handling field 37 at the left side of the ridge 36 but to the right handling field 38 then a change in the function will take place in case of the displacement of the front handling field 32 or 35 the control of a movement along the direction z will take place which is an upward or downward movement and it is normal to the control made in the previous case.

The solution shown in FIGS. 16 to 18 does not have the essence in any particular image control mode but in addition to moving a finger along the sensing handling surface in addition to conventional controls further control dimensions will be provided. For attaining this, the handling field itself has to be moved with respect to the body of the device and two further functions can be added to these possibilities by touching an appropriate field at the rear side of the device which can be carried out by the fingers holding the device at the rear side without the danger of dropping.

Figure 19:
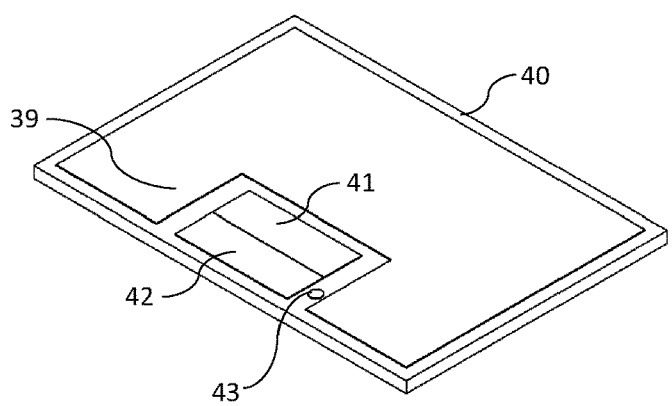
FIG. 19 shows the sketch of the plate plane of a laptop or desktop device.
Figure 20:
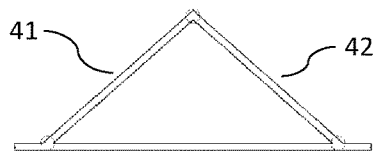
FIG. 20 shows the two handling fields extending out upwardly from the upper plane of the device shown in FIG. 19.

Finally, reference is made to FIGS. 19 and 20. FIG. 19 shows the top view of a conventional laptop 40 or similar computer, wherein the keyboard is symbolized by area 39, and in front of it a substantially rectangular field is provided for a conventional touch pad as a cursor control field. According to the invention the enhanced function of the handling field is provided in such a way that in the given area two handling fields 41, 42 are provided which can be angularly turned out with respect to each other. In the initial or basic position these fields are arranged in the upper plane of the laptop 40 and in spite of being divided in two parts they can be used for the conventional cursor control function. Beside the handling fields 41, 42 a button 43 or a similar means is provided and as a result of the pressing of the button 43 the two handling fields 41, 42 (owing to a spring bias) will swell out from the upper plane and will take the position shown in FIG. 20. Guiding elements not shown in the drawing make sure that this inclined position of the handling fields 41, 42 is kept in a stable way. In this elevated position the role of the handling fields 41, 42 will be separate and they will assume the functions of the handling fields 1, 2 as described in connection with the description of the smart watch 10 in connection with FIGS. 1 to 12. Because the two handling fields 41, 42 are now separated and have respective different inclined planes, the same functions can be realized by them what have been described in connection with the control of the smart watch 10. Although the angularly inclined design is preferred, an alternative solution can also be realized in which a rectangular support element takes an upright position relative to the upper plane, and the handling fields are provided on the front and rear faces on this plate.

The invention is not limited to any one of the exemplary embodiments shown because its essence lies in the substantial enhancement and simplification of the handling functions, whereas it solves tasks that have appeared up to the present as unsolvable e.g. a device having such a small handling field as the smart watch 10 will not only have the handling possibility of laptops or mobile phones but considering their functions it can provide excess services with respect to such devices.

The invention claimed is:

1. Arrangement for the controlled manual adjustment by finger movements in three dimensions of display parameters of an image to be shown on a display of a smart electronic device, said smart electronic device being strapped around the wrist in the manner of a watch or a similar device that comprises:
   a device body comprising said display, said display being positioned on a top surface of the body;
   a strap connecting two opposite sides of the device body;
   a first handling field arranged on a side of said body said handling field being configured and dimensioned to have a two-dimensional touch sensitive surface oriented at an angle to the display to be touched by a first finger of a hand of a user, whereby a first predetermined group of display parameters can be controlled;
   a second handling field arranged at an opposite side of said body, said second handling field being a two-dimensional touch sensitive surface and being positioned and configured to be touched by a second finger of the same hand, said second finger adjusting on said second handling field during movement at least one further display parameter that does not belong to the first group, wherein said first and second handling fields define respective inclined planes which are spaced from each other, and
   wherein said first and second handling fields are controlled by respective two dimensional movement directions (x, y) of which a first direction (x) in the first handling field is roughly parallel to the first direction (x) in the second handling field, whereby finger movement on the first or second handling field controls the image in two dimensions, whereas by simultaneous finger movement on the two handling fields by the first and second fingers of the same hand the user can control display parameters in a third direction (z), whereby the displayed image can be controlled in three dimensions defined by the possible pairs of directions (x, y), (x, z) and (y, z), and the simultaneous movement resembling natural movements for the user.

2. The arrangement as claimed in claim 1, wherein said smart electronic device is a smart watch.

3. The arrangement as claimed in claim 1, wherein at least a part of said first handling field can be moved relative to the body along a closed path in two mutually normal directions, and such a movement of the handling field constitutes in a first functional mode an element of an in itself known data entry device, and in a different other functional mode such movement relative to the body is associated with said control of said first predetermined group of display parameters.

4. The arrangement as claimed in claim 1, wherein the first handling field is substantially smaller than said second handling field.

5. Arrangement for the controlled manual selection of an image or the manual adjustment of the display parameters of the image to be shown on a display in a vehicle equipped with a smart electronic device that comprises:
   a steering wheel in said vehicle with a connection member to a central column;
   a first handling field arranged on an outer side region of said connection member, said first handling field facing the driver and can be easily reached by the thumb of the driver when grasping said steering wheel and having a two-dimensional touch sensitive surface and by the touching of the first handling field a first predetermined group of display parameters can be controlled;
   a second handling field arranged at a rear side of said connecting member behind said first handling field that can be reached and touched easily by at least one second finger of the same hand of the driver and having a two-dimensional touch sensitive surface, whereby at least one further display parameter can be adjusted that does not belong to the first group, wherein said finger movements along said two-dimensional touch sensitive fields have respective coordinates in a first direction (x) and a direction normal to the first direction (y), of which at least either the first or the second directions are roughly parallel to each other,
   wherein the simultaneous movement of said thumb and second finger along said first and second handling fields in a direction normal to the direction of said roughly parallel coordinates corresponds to the control of said image along the third coordinate (z).

6. The arrangement as claimed in claim 5, wherein at least a part of said first handling field can be moved relative to the steering wheel along a closed path in two mutually normal directions, and such a movement of the handling field constitutes in a first functional mode an element of an in itself known data entry device, and in a different other functional mode such movement relative to the body is associated with said control of said first predetermined group of display parameters.

7. Arrangement for the controlled manual selection of an image or the manual adjustment of the display parameters of the image to be shown on a display of a smart electronic device that comprises:
   a flat body having a front and a rear face;
   a display arranged at the front face;
   first handling field arranged on a part of the front face away from the display, said first handling field having a two-dimensional touch sensitive surface that can be easily reached by a first finger of a hand of a user holding the smart electronic device and by the touching of the first handling field by said first finger a first predetermined group of display parameters can be controlled;

a second handling field arranged at said rear side of said body having a two-dimensional touch sensitive surface and can be reached and touched easily by a second finger of the same hand of the user, whereby at least one further display parameter can be adjusted that does not belong to the first group, wherein movements on said two-dimensional touch sensitive surfaces have respective coordinates in a first direction (x) and a direction normal to the first direction (y), of which at least either the first or the second directions are roughly parallel to each other, wherein the simultaneous movement of said thumb and second finger along said first and second handling fields in a direction normal to the direction of said parallel coordinates (x) corresponds to the control of said image along the third coordinate (z).

8. The arrangement as claimed in claim 7, wherein at least a part of said first handling field can be moved relative to said body along a closed path in two mutually normal directions, and such a movement of the first handling field constitutes in a first functional mode an element of an in itself known data entry device, and in a different other functional mode such movement relative to the body is associated with said control of said first predetermined group of display parameters.

9. Arrangement for the controlled manual selection of an image or the manual adjustment of the display parameters of the image to be shown on a display of a laptop or a similar computer that comprises:

a flat body having a flat area for a keyboard;

a display;

an area adjacent to the keyboard;

a first and a second handling field arranged in said adjacent areas, said handling fields are made as respective spaced touch sensitive areas having respective two-dimensional touch sensitive surfaces, and they can be raised out of the flat area of the keyboard to close an angle with each other or being parallel with each other and normal to the flat area, said first and second handling fields can be touched by respective first and second fingers of a hand of a user;

when the first handling field is touched by said first finger a first predetermined group of display parameters can be controlled thereby;

when the second handling field is touched by the second finger of the user, at least one further display parameter can be adjusted that does not belong to the first group, wherein said two-dimensional movements have respective coordinates in a first direction (x) and a direction normal to the first direction (y), of which at least either the first or the second directions are roughly parallel to each other, wherein the simultaneous movement of said thumb and second finger along said first and second handling fields in a direction normal to the direction of said parallel coordinates corresponds to the control of said image along the third coordinate (z).

10. The arrangement as claimed in claim 9, wherein said touch sensitive areas are respective front and rear surfaces of a structure comprising two flat bodies that can be raised out of said adjacent area and said bodies are inclined towards each other.

* * * * *